United States Patent
Schroeder

(10) Patent No.: US 8,912,805 B2
(45) Date of Patent: Dec. 16, 2014

(54) DEVICE AND METHOD FOR PROCESSING AND MEASURING PROPERTIES OF A MOVING ROD OF MATERIAL

(75) Inventor: Dierk Schroeder, Hamburg (DE)

(73) Assignee: Hauni Maschinenbau AG, Hamburg (DE)

(*) Notice: Subject to any disclaimer, the term of this patent is extended or adjusted under 35 U.S.C. 154(b) by 401 days.

(21) Appl. No.: 13/241,943

(22) Filed: Sep. 23, 2011

(65) Prior Publication Data
US 2012/0074958 A1 Mar. 29, 2012

(30) Foreign Application Priority Data
Sep. 28, 2010 (DE) .......... 10 2010 041 571

(51) Int. Cl.
*G01N 22/00* (2006.01)
*A24C 5/34* (2006.01)
(52) U.S. Cl.
CPC ............. *G01N 22/00* (2013.01); *Y10S 131/906* (2013.01)
USPC ........... 324/637; 324/636; 324/639; 324/642; 131/906
(58) Field of Classification Search
CPC .............. A24C 1/00; A24C 1/02; A24C 5/14; A24C 5/34; G01N 22/00; G01N 22/02; G01N 22/04
USPC .......... 324/633–648; 131/905, 906, 908, 84.1
See application file for complete search history.

(56) References Cited

U.S. PATENT DOCUMENTS 3,283,261 A * 11/1966 Buck .................................. 331/9
4,381,485 A    4/1983 Steinbrecher
4,464,770 A * 8/1984 Maurer et al. ................. 375/373
4,675,595 A * 6/1987 Hane ............................. 324/640
4,733,165 A * 3/1988 Richardson et al. .......... 324/636
5,177,444 A * 1/1993 Cutmore ....................... 324/637

(Continued)

FOREIGN PATENT DOCUMENTS

DE    40 04 119      8/1991
DE    197 34 978     2/1999

(Continued)

OTHER PUBLICATIONS

German Office Action dated Aug. 11, 2011 in counterpart German Application No. 10 2010 041 571.5.

(Continued)

*Primary Examiner* — Vinh Nguyen
*Assistant Examiner* — James Split
(74) *Attorney, Agent, or Firm* — Greenblum & Bernstein, P.L.C.

(57) ABSTRACT

Device for processing and measuring properties of a moving rod of material of the tobacco processing industry includes a microwave resonator structured and arranged so that the rod of material is conveyable through the microwave resonator. Includes microwave generator with output frequency $f_0$, and frequency stabilized oscillator to generate intermediate frequency $f_{IM}$ that is less than $f_0$. Single sideband modulator supplies microwave resonator with a sideband signal having a sideband frequency shifted with respect to output frequency $f_0$ by intermediate frequency $f_{IM}$, and at least one analysis arrangement includes single sideband demodulator, low-pass filter, and analog to digital converter arranged in series. Single sideband demodulator receives a measurement signal of the sideband frequency transmitted or reflected from the microwave resonator, and receives output frequency $f_0$. Low-pass filter passes an output signal of single sideband demodulator with intermediate frequency $f_{IM}$, and filters out higher frequency signal portions.

14 Claims, 7 Drawing Sheets

(56) References Cited

U.S. PATENT DOCUMENTS

| | | | |
|---|---|---|---|
| 5,315,258 A * | 5/1994 | Jakkula et al. | 324/640 |
| 5,333,493 A * | 8/1994 | Cutmore | 73/73 |
| 5,397,993 A * | 3/1995 | Tews et al. | 324/634 |
| 5,841,288 A * | 11/1998 | Meaney et al. | 324/639 |
| 6,121,595 A * | 9/2000 | Lewis et al. | 219/695 |
| 6,163,158 A | 12/2000 | Moeller et al. | |
| 6,204,813 B1 * | 3/2001 | Wadell et al. | 342/463 |
| 6,452,404 B2 * | 9/2002 | Moeller et al. | 324/633 |
| 6,608,683 B1 * | 8/2003 | Pilgrim et al. | 356/432 |
| 6,842,010 B2 * | 1/2005 | Biernacki | 324/637 |
| 6,859,046 B2 * | 2/2005 | Schajer | 324/637 |
| 6,922,061 B2 * | 7/2005 | Herrmann et al. | 324/633 |
| 7,031,862 B2 * | 4/2006 | Miljak | 702/100 |
| 7,079,596 B1 * | 7/2006 | Namura | 375/324 |
| 8,280,340 B2 * | 10/2012 | Xuan et al. | 455/333 |
| 2005/0225332 A1 | 10/2005 | Schroder | |
| 2008/0319285 A1 * | 12/2008 | Hancock | 600/309 |
| 2009/0033339 A1 * | 2/2009 | Clunn | 324/642 |
| 2012/0074957 A1 | 3/2012 | Schroeder | |

FOREIGN PATENT DOCUMENTS

| | | |
|---|---|---|
| DE | 44 31 589 | 6/1999 |
| DE | 10 2004 017 597 | 6/2006 |
| EP | 0 791 823 | 8/1997 |
| EP | 2 433 510 | 3/2012 |

OTHER PUBLICATIONS

A. L. Cullen et al., "New System for microwave Q-factor measurement", Microwaves, Optics and Acoustics, vol. 2, No. 3, May 1978, pp. 77-84.

J. M. Catala-Civera et al., "Microwave Non-Destructive Evaluation of Moisture Content in Liquid Composites in a Cylindrical Cavity at a Single Frequency", Advances in Microwave and Radio Frequency Processing—8th International Conference on Microwave and High-Frequency Heating, Jan. 2006, pp. 138-148.

Tobias Hermann et al., "A Novel System for Real-time Measurement of the Electrical Properties of a Cavity Resonator", Proceedings of the 38th European Microwave Conference, 2008, pp. 67-70.

A. L. Cullen, "Millimeter-Wave Open-Reesonator Techniques ", Infrared and Millimeter Waves, vol. 10, 1983, pp. 272-281.

L. J. Swenson et al., "A Fast, Ultra-Sensitive and Scalable Detection platform Based on Superconducting Resonators for Fundamental Condensed-Matter and Astronomical Measurements", Low Temperature Detectors LTD, Proceedings of the 13th International Workshop, 2009, pp. 84-87.

Paul Horowitz et al., "Chapter 13—High Frequency and High-Speed Techniques", The Art of Electronics, Jan. 1989, pp. 895-898.

Benjamin A. Mazin et al., "Digital readouts for large microwave low-temperature detector arrays", Nuclear Instruments and Methods in Physics Research, 2006, pp. 799-801.

Bourdel E et al., "Measurement of the Specific Mass and the Humidity Ratio of Cigarettes", European Microwave Conference, 1998, 28th, IEEE, Piscataway, NJ, USA, XP031067063 , Oct. 1, 1998, pp. 689-694.

Nyfords et al., "Industrial Microwave Sensors", Artech House, XP002334964 , Jan. 1, 1989.

Dabrowski, "Intro to RF Front—End Design", XP055091845, URL:http://www.ek.isy.liu.se/~jdab/RTxArch.pdf, Nov. 1, 2005, pp. 1-14.

Schiek, "Grundlagen der Hochfrequenzmesstechnik", Springer, Berlin, XP055091691, Jan. 1, 1999.

Schilcher, "RF applications in digital signal processing", Cern Accelerator School on Digital Signal Processing, CAS 2007—SIGTUNA, XP055091831, Jan. 1, 2008, pp. 249-283.

"Making Stimulus/Response Measurements Using the Agilent N9322C Basic Spectrum Analyzer and Tracking Generator", XP55091648, URL:http://cp.literature.agilent.com/litweb/pdf/5991-1877EN.pdf, (downloaded Mar. 14, 2013).

European Search Report conducted in counterpart European Appln. No. 111 81 347.3 (Dec. 17, 2013).

* cited by examiner

DEVICE AND METHOD FOR PROCESSING AND MEASURING PROPERTIES OF A MOVING ROD OF MATERIAL

CROSS-REFERENCE TO RELATED APPLICATIONS

The present application claims priority under 35 U.S.C. §119(a) of German Patent Application No. 10 2010 041 571.5 filed Sep. 28, 2010, the disclosure of which is expressly incorporated by reference herein in its entirety.

BACKGROUND OF THE INVENTION

1. Field of the Invention

The invention relates to a device for processing and measuring properties of a moving rod of material in the tobacco processing industry comprising a microwave measurement device, which has a microwave resonator through which the rod of material is conveyed or can be conveyed, and a microwave generator having an output frequency $f_0$. The invention further relates to a microwave measurement device for a corresponding device and a method for processing and measuring of properties of a moving rod of material, particularly of the tobacco processing industry, that is conveyed through a microwave resonator, wherein an output frequency $f_0$ is generated.

The invention relates, in particular, to the field of rod formation and rod processing in the tobacco processing industry, that is, the creation of endless cigarette rods and endless filter rods in rod making machines. For example, an endless cigarette rod is created by initially showering tobacco onto a rod conveyor, then enclosing the endless rod of tobacco with a strip of cigarette paper, and then cutting cigarettes of multiple use lengths from the endless rod of tobacco. Forming the endless rod of tobacco or endless filters and the subsequently cutting, or cutting to length, of the rod occurs at high speed. With present day cigarette and filter manufacturing machines, rod speeds are typically 10 m/s, wherein with section lengths of 100 mm, there are 100 cutting cycles per second.

2. Discussion of Background Information

The quality of the cigarettes depends on the state of the tobacco in the endless tobacco rod. For this reason, the moisture and the density of the tobacco in the endless cigarette rod are measured, and the density, in particular, is controlled. Furthermore, the case of sudden or transient signal fluctuations suggests the presence of foreign bodies, wherein the corresponding rod sections are subsequently sorted out.

In modern cigarette manufacturing machines, this occurs using microwave measurement devices that have at least one microwave resonator housing, through which the endless rod of tobacco passes, as is disclosed in the document DE 10 2004 017 597 B4 (and in counterpart U.S. Publication No. 2005/0225332), for example, the disclosures of which are expressly incorporated by reference herein in their entireties. That document discloses a resonator housing with a resonator cavity in the form of a hollow cylinder that is disposed symmetrically to the endless cigarette rod. It provides a coupling in antenna and a coupling out antenna, using which a microwave signal is coupled for inducing into the resonator cavity an oscillation, and a transmitted part is coupled out in turn.

The measurement using a microwave resonator utilizes the physical fact that the resonance curve of the microwave field in the microwave resonator changes with the presence of a rod of material in the microwave resonator. In principle, the complex dielectric constant of the rod of material guided through the resonator is measured. The complex dielectric constant has a real part and an imaginary part, or a magnitude and a phase. The information about the density and the moisture content of the rod are contained in the two parameters of the complex dielectric constant. Changes in the density or moisture content lead to the characteristic change of the two parameters, and with it, to the resonance curve of the microwave resonator.

Compared to the unloaded microwave resonator, the maximum or minimum of a resonance curve shifts to lower frequencies in the presence of a rod of material. In addition, the resonance curve broadens. Changes in the density and changes in the moisture of the rod of material respectively create their own specific changes of the position, height and width of the resonance curve. If at least two measurement variables of the resonance curve are measured, the density and the moisture can be determined independent of each other within the scope of the measurement accuracy and of the correlations of the functional dependencies of the measurement variables from the rod density and rod moisture.

An evaluation circuit for evaluating a microwave resonator-measurement signal is known from the document EP 0 791 823 A2 (and its counterpart U.S. Pat. No. 6,163,158), the disclosures of which are expressly incorporated by reference herein in their entireties. Multiple independent measurement variables are created, in that microwaves with at least two different frequencies, with which a part of the resonance curve is sampled, are supplied to the resonator. Shifts of the resonance are captured by comparison of the resonance curves of the resonator influenced by the material and uninfluenced by material, and the damping is captured by comparison of the amplitudes of the resonator curves at the frequencies of the supplied microwaves. The density and the moisture of the endless rod of tobacco are reconstructed from the amplitude of the measured signals and the gradient of the slope.

The fundamental frequency of the microwave signal is adjusted with respect to the resonance curve for the unloaded microwave resonator so that it is located at the inflection point of one of the slopes of the resonance curve. The at least two modulated frequencies lie above and below the inflection point on the same slope. In a numerical example, 5.79 GHz and 5.81 GHz, that is 5.8 GHz±10 MHz, are named as input frequencies. Switching between the two frequencies occurs every 5 µs, i.e. a frequency of 100 kHz. The microwave output signal is rectified via a circulator and a microwave diode, and further led via an analog to digital converter to an evaluation arrangement.

In practice, this procedure is limited. For measuring on a slope of a resonance curve the measurement is performed at a fixed working frequency, preferably at the point of inflection of the slope of the resonance of the unloaded resonator. In the case of comparatively small quantities of material in the resonator, only small signal changes are observed, whereas with large quantities of material, there are large changes of the signal, which can also lead to oversteering the signal. Small signal changes imply poor accuracy of the measurement and poor discrimination of the rod density and moisture. Therefore, the occurring small signal changes with which the system must still function reliably, represent a high demand for accuracy on the microwave signal processing. Due to this high demand, all components must be produced and assembled with very high accuracy, which results in correspondingly high costs.

Also due to the small signal changes, small changes or drifts of the characteristic values of the microwave circuit components, which can arise due to component aging or temperature fluctuations and other external changes for example, impact the measurement accuracy. Consequently, the exact calibration of the system must be checked frequently, and if necessary, must be repeated.

With the known measurement method, the microwave signals must be rectified. This is performed using microwave diodes, in particular, Schottky diodes. These diodes have individual non-linear and temperature dependent characteristic curves which cause systematic measurement inaccuracies that can be only partially corrected based on temperature measurements. This fact limits the measurement accuracy and requires an individual compensation.

Independent of this, with measurements using a microwave resonator outside of the resonance frequency it must be observed that the shape of the electrical field used for the measurement is not aligned ideally axially outside of the resonance frequency, but rather diagonally in the resonator, and in the shape of the field is also dependent on the fill level, rod density and rod moisture. Consequently, the measurement accuracy is position dependent. For foreign body detection based on the microwave measurement, the reliability of detecting foreign bodies possibly present in the rod of material therefore depends on the position in the rod.

SUMMARY OF THE EMBODIMENTS

Therefore, in contrast to the prior art, embodiments of the present invention are directed to a device, a measurement device and a method for processing and measuring properties of a rod of material, in particular, in the tobacco processing industry, moved or moving along its longitudinal axis at high speed, with which the previously stated accuracy requirements can be maintained better than before.

Accordingly, embodiments are directed to a device for processing and measuring properties of a rod of material, in particular of the tobacco processing industry, that can be moved or is moving along the longitudinal axis. The device includes a microwave measurement device, which has a microwave resonator through which the endless rod of material is conveyed or can be conveyed, and a microwave generator having an output frequency ($f_0$). The microwave resonator is supplied or can be supplied via a single sideband modulator with a sideband signal whose sideband frequency ($f_0+f_{IM}$ or $f_0-f_{IM}$) is shifted compared to the output frequency $f_0$ by an intermediate frequency ($f_{IM}$) that is generated by a frequency stabilized oscillator and is less than $f_0$. At least one analysis arrangement is provided that includes a connection in series of a single sideband demodulator, a low-pass filter, and an analog to digital converter. The single sideband demodulator is supplied or can be supplied with a measurement signal of the sideband frequency ($f_0+f_{IM}$ or $f_0-f_{IM}$) transmitted or reflected by the microwave resonator, and with the output frequency ($f_0$). The low-pass filter is designed to allow the passage of the output signal of the single sideband demodulator with the intermediate frequency ($f_{IM}$) and to filter out higher frequency signal portions.

Embodiments of the invention is based on the fundamental idea that in the device according to the invention, using a single-sideband method, the reflected or transmitted measurement signal is modulated down to the intermediate frequency $f_{IM}$ while maintaining its amplitude and phase. The intermediate frequency $f_{IM}$ is not within the microwave range, rather it has a substantially lower frequency, in particular between 1 MHz and 100 MHz, preferably between 5 and 20 MHz. This signal, in contrast to the microwave signal which has, e.g., a frequency of approximately 6 GHz, can be fed directly to the analog to digital conversion with available fast A/D converters so that nonlinearities of analog components that are generated by a microwave diode, are avoided. Due to the correspondingly larger signal amplitude, drift and tolerance influences are minimized and, therefore, cycle times between system checks and recalibration are increased.

The processing of the rod of material can be the production of an endless cigarette rod or an endless filter rod, the addition of additives, wrapping the rod with a wrapping paper and/or cutting cigarettes or filter plugs for example, or even producing a rod from textile fibers and the stretching of the rod. The measurement results can be used for the purpose of controlling the production process and/or the processing process so that a uniform rod density and rod moisture are attained, or so that parts of the rod, whose density or moisture lie outside of specified parameters are eliminated from the further processing.

The resonance behavior of the resonator can be measured in a reflection arrangement in which only one port is used at the resonator for coupling in a microwave signal and for the measurement, or in a transmission arrangement in which one port is used at the microwave resonator for coupling in and a further port is used for the measurement of the transmitted signal. In microwave technology, the transmission and reflection behavior of resonators is described by scattering parameters, the so-called "S parameters". With these, the $S_{11}$ parameter describes the reflection at the input port of the resonator depending on the frequency, and the $S_{21}$ parameter describes the transmission properties from the input port to the output port. Both S parameters are complex value functions of the frequency and of the complex value dielectric constant of the rod. The S parameters can be represented as a real part and an imaginary part, or as a magnitude and phase. In the latter named case, changes in the density or moisture content of the rod cause changes of the magnitude and phase of the S parameters of the resonator.

In the single sideband modulation method used according to the invention, a frequency mixture of signals that is composed of the fundamental frequency $f_0$ and the sidebands $f_0+f_{IM}$ as the upper sideband and $f_0-f_{IM}$ as the lower sideband are created by mixing a harmonic microwave oscillation $f_0$ with a lower frequency harmonic signal $f_{IM}$. Due to the single sideband modulation method with suppressed carriers known in high-frequency technology, it is achieved that only either the upper sideband or the lower sideband respectively remains from the frequency mixture, in each case without a carrier signal.

During the demodulation, the remaining sideband is modulated with the fundamental frequency $f_0$, whereby a signal with intermediate frequency $f_{IM}$ arises whose amplitude and phase contain those of the generating frequencies $f_0 \pm f_{IM}$ and $f_0$, which can therefore be reconstructed from the intermediate frequency signal. Within the stability of the base signal $f_0$, changes of the amplitude and phase of the intermediate frequency signal therefore originate in changes of the signal transmitted or reflected by the microwave resonator.

Preferably, at least two analysis arrangements, in particular of the same kind, are provided each with a connection in series comprising at least one single sideband demodulator, a low-pass filter and an analog to digital converter. One analysis arrangement receives a measurement signal transmitted by the microwave resonator and the other analysis arrangement receives a measurement signal reflected by the microwave resonator. In this manner, in particular, via the same type of analysis arrangements, both the $S_{21}$ as well as the $S_{11}$ parameters can be measured using the single sideband modulation method used according to the invention. The large number of measurement values permits a further increase of the accuracy for determining the density and moisture of the rod of material. Both analysis arrangements are preferably led to a downstream common evaluation device.

An insulator, a circulator, a directional coupler and/or another signal divider is/are advantageously disposed between the single sideband modulator and the microwave resonator. These components prevent, among others, the disruption of the generator by reflected microwave power.

If advantageously a further analysis arrangement is provided, in particular of the same type with a connection in series comprising a single sideband demodulator, a low-pass filter and an analog to digital converter, that receives a decoupled part of the unmodulated sideband signal via the circulator, insulator, directional coupler and/or another signal divider disposed on the input side. Then a signal is available with which it is possible to directly compare the input and output signals according to the magnitude and phase, in particular by way of a downstream common evaluation device. In addition, drift in the amplitude and/or the phase of the output signal can thereby be compensated.

Preferably, the analysis arrangements with the connections in series are of the same type in each case, so that direct comparisons are possible. Being of the same type, in particular, that the low-pass filter has the same filter characteristics and the analog to digital converters are matched to each other, in particular, their threshold values and dynamic ranges and factors.

In an advantageous further development, a control device is provided by which the output frequency $f_0$ can be controlled so that the sideband frequency $f_0+f_{IM}$ or $f_0-f_{IM}$ is tracked to a present or current resonance frequency in the microwave resonator. The tracking of the sideband frequency, which is supplied to the microwave resonator, after the present resonance frequency in the microwave resonator has several advantages. At resonance, the shape of the electrical field used for the measurement is ideally aligned axially so that the measurement accuracy is no longer dependent on the location or position. Therefore, foreign bodies in the rod for example, can be easily detected independent of their position. Furthermore, the microwave amplitude of the transmitted signal is at its respective maximum at resonance for any amount of attenuation in the resonator. In this way, error influences due to component influences are minimized. A further advantage consists in that processing can be performed over greater measurement ranges without system conversion.

Because the control unit carries out frequency tracking based on the measured values of the analog to digital converter arriving in real time, a quasi-continuous and quasi-instantaneous frequency tracking is possible that also has a minimum time delay.

In one preferred embodiment, the control unit is designed to use the value of the phase and/or the amplitude of the transmitted or reflected signal as a controlled variable. A value of the phase equal to zero and/or an amplitude maximum or an amplitude minimum is aimed for. At resonance, the phases of both transmitted signals as well as the reflected signals have a zero crossing. In the presence of a rod of material in the resonator, the frequency response curves of both phases are largely linear around the zero crossing. For this reason, the phases or the zero crossings of the phases are well-suited as control variables for the frequency tracking. The information about the phase is available in fractions of a millisecond so that a tracking of the frequency coupled into the microwave resonator after the resonance frequency occurs quasi-instantaneously. In this space of time, an endless rod of tobacco is further moved only by a fraction of a millimeter.

In a preferred further development, a digital signal generation device is provided as a microwave generator for generating an output frequency $f_0$, by direct digital synthesis (DDS). The single sideband modulator is designed as an I/Q modulator, and the single sideband demodulator is designed as an I/Q demodulator, and a digital to analog converter is provided for generating two signals that are shifted by 90° to each other for the intermediate frequency $f_{IM}$. Thus, the signal generation for both microwaves as well as the intermediate frequency signal is attained by the digital to analog conversion, wherein I/Q modulation and I/Q demodulation represent a very robust and interference tolerant method.

Advantageously, an evaluation device for evaluating the output signals of the analog to digital converter(s) is provided, wherein, in particular, the evaluation device is integrated into the control device. Preferably, the evaluation device is downstream and common to the analog to digital converters.

Embodiments of the invention is also solved by a microwave measurement device for a device for processing and measuring properties of a moved or moving rod of material of the tobacco processing industry, as described above, having a microwave resonator through which the rod of material is conveyed or can be conveyed, and a microwave generator with an output frequency $f_0$. The microwave resonator is supplied or can be supplied via a single sideband modulator with a sideband signal, whose sideband frequency $f_0+f_{IM}$ or $f_0-f_{IM}$ is shifted with respect to the output frequency $f_0$ by an intermediate frequency $f_{IM}$, generated by a frequency stabilized oscillator, which is smaller than $f_0$. At least one analysis arrangement is provided that includes a connection in series of a single sideband demodulator, a low-pass filter and an analog to digital converter. The single sideband demodulator is supplied or can be supplied on the one hand with a measurement signal of the sideband frequency $f_0+f_{IM}$ or $f_0-f_{IM}$ transmitted or reflected by the microwave resonator and on the other hand with the output frequency $f_0$. The low-pass filter is designed to pass an output signal of the single sideband demodulator with the intermediate frequency $f_{IM}$, and filter out higher frequency signal portions.

The microwave measurement device has same properties, features and advantages as the device according to the invention.

Finally, embodiments of the invention are also solved by a method for processing and measuring properties of a moved or moving rod of material of the tobacco processing industry which is conveyed through a microwave resonator. An output frequency $f_0$ is generated, that is further developed in that the output frequency $f_0$ is modulated in a single sideband modulator with an intermediate frequency $f_{IM}$ that is less than $f_0$, and a sideband signal with a sideband frequency $f_0+f_{IM}$ or $f_0-f_{IM}$ is supplied into the microwave resonator, in particular via an insulator, circulator, directional coupler and/or another signal divider. The signal of the sideband frequency $f_0+f_{IM}$ or $f_0-f_{IM}$ reflected and/or transmitted from the microwave resonator is modulated in a single sideband demodulator with a signal of the output frequency $f_0$. In a low-pass filter, a portion with the intermediate frequency $f_{IM}$ of the measurement signal is passed through to an analog to digital converter, while higher frequency signal portions are filtered out.

This method corresponds to the method performed in the device according to the invention and the measurement device according to the invention. The method also offers the advantages according to the invention, in particular independence from non-linear characteristic curves of analog components, such as Schottky diodes, and from the insensitivity resulting therefrom with respect to the lack of accuracy at small signal amplitudes. The method according to the invention yields the data from which the scattering parameters $S_{11}$ and/or $S_{21}$ are measured according to their amplitude and/or phase or their real part and/or imaginary part. Amplitudes and phases are contained in a signal of the comparatively low intermediate frequency $f_{IM}$ which can be processed by a direct analog to digital conversion so that the digital output values already contain the necessary information about amplitude and phase.

Preferably, a sideband signal of the sideband frequency $f_0+f_{IM}$ or $f_0-f_{IM}$ shielded from the microwave resonator by an insulator, a circulator, a directional coupler and/or another signal divider is modulated down to the intermediate frequency $f_{IM}$ by way of single sideband modulation with the output frequency $f_0$, and transmitted via a low-pass filter to an analog to digital converter. This means that the output sideband signal that is not disrupted by signal parts reflected by the microwave resonator is present digitally as a direct reference value, and serves as a comparison value for the measurement signals of the reflected and/or transmitted signals. In the process, at the location at which this sideband signal is tapped, the signal is shielded from reflected signals via the insulator or circulator.

Preferably, both the analog to digital converter(s) as well as an oscillator that generates the intermediate frequency $f_{IM}$ are synchronized to a frequency stabilized time signal. This has the consequence that the phase position of the sampling of the output signal modulated down to the intermediate frequency $f_{IM}$ is synchronized to its phase so that at any time the phase of the signal can be determined with high accuracy. Incorrect measurements of the phase due to phase shifts between the generation of the intermediate frequency $f_{IM}$ and sampling are thus excluded.

In a preferred further development it is provided that a control of the sideband frequency is carried out to a present resonance frequency in the microwave resonator. In the process, the output frequency $f_0$ is preferably adjusted. Then, the intermediate frequency $f_{IM}$, in particular, is held constant.

In a preferred alternative, the control is carried out using a phase of a transmitted signal, wherein a phase value of zero, in particular, is aimed for. This corresponds to the control already described above, based on the zero crossing of the frequency-response curve of the phase of the $S_{11}$ component or the $S_{21}$ component. This alternative is very accurate and very fast.

Alternatively, it is provided that the control is carried out using the position of a maximum or minimum of a transmitted and/or reflected signal. For this purpose, the output frequency is preferably switched periodically between two values that are adapted so that the sideband frequency lies alternatingly above and below the resonance maximum or minimum. It is advantageous to aim to attain the same signal amplitude for both frequencies. In this case, the switching of the frequency is carried out based on the output frequency $f_0$, whereas the intermediate frequency $f_{IM}$ remains constant. Alternatively, a value of zero for the slope of the resonance curve is also advantageously aimed for.

The single sideband modulation and single sideband demodulation then result in a signal with a constant frequency $f_{IM}$, which changes its amplitude and phase in cycle with the switching of the frequency $f_0$. The control variable in this case is a minimal or vanishing difference of the amplitude in the two cases. Because a drift of the resonance frequency leads to a characteristic difference between the amplitudes at the two frequencies, which is positive or negative, this control variable is also well-suited for tracking the excitation frequency according to the resonance frequency in the microwave resonator.

An alternative control advantageously provides for controlling to a maximum signal amplitude with a measurement of the $S_{21}$ parameter, and/or controlling to a minimum signal amplitude with a measurement of the $S_{11}$ parameter.

The features, properties and advantages named with the different subject matters of the invention, i.e., with the device according to the invention, the measurement device according to the invention and the method according to the invention, apply in each case without restriction also to the respective other subject matters according to the invention. Thus, the further features, and where applicable dependent claims among others, named with the device according to the invention, can also be used in advantageous further developments of the measurement device according to the invention.

Embodiments of the invention are directed to a device for processing and measuring properties of a moving rod of material of the tobacco processing industry that includes a microwave measurement device. The device includes a microwave resonator structured and arranged so that the rod of material is conveyable through the microwave resonator, a microwave generator with an output frequency $f_0$, and a frequency stabilized oscillator structured and arranged to generate an intermediate frequency $f_{IM}$ that is less than $f_0$. A single sideband modulator is structured and arranged to supply the microwave resonator with a sideband signal having a sideband frequency shifted with respect to the output frequency $f_0$ by the intermediate frequency $f_{IM}$, and at least one analysis arrangement includes a single sideband demodulator, a low-pass filter, and an analog to digital converter arranged in series. The single sideband demodulator is coupled to receive a measurement signal of the sideband frequency one of transmitted or reflected from the microwave resonator, and to receive the output frequency $f_0$, and the low-pass filter is structured and arranged to pass an output signal of the single sideband demodulator with the intermediate frequency $f_{IM}$, and to filter out higher frequency signal portions.

According to embodiments of the invention, the at least one analysis arrangement can include at least two analysis arrangements, each of the at least two analysis arrangements having a single sideband demodulator, a low-pass filter, and an analog to digital converter arranged in series. A first of the at least two analysis arrangements is structured and arranged to receive a measurement signal transmitted by the microwave resonator, and a second of the at least two analysis arrangements is structured and arranged to receive a measurement signal reflected by the microwave resonator.

In accordance with other embodiments, at least one of an insulator, a circulator, a directional coupler, and a signal divider can be disposed between the single sideband modulator and the microwave resonator. Further, another analysis arrangement can include a single sideband demodulator, a low-pass filter, and an analog to digital converter arranged in series, and the another analysis arrangement may be structured and arranged to receive a decoupled part of an unmodulated sideband signal via the at least one of the circulator, the insulator, the directional coupler, and the signal divider.

According to still other embodiments, a control device may be structured and arranged to control the output frequency $f_0$ so that the single sideband frequency tracks a present resonance frequency in the microwave resonator. The control device can utilize as a control variable at least one of a phase value and an amplitude of the transmitted or reflected signal, wherein a target for the control variable is at least one of a phase value of zero and an amplitude maximum or an amplitude minimum.

Further, the microwave generator can include a digital signal generating device structured and arranged to generate the output frequency $f_0$ by direct digital synthesis. The single sideband modulator may include an I/Q modulator, the single sideband demodulator can include an I/Q demodulator, and the frequency stabilized oscillator can include a digital to analog converter structured and arranged to generate two signals shifted from each other by 90° for the intermediate frequency $f_{IM}$.

In accordance with further embodiments, an evaluation device is structured and arranged to evaluate output signals of the analog to digital converter.

Moreover, the control device may include an evaluation device structured and arranged to evaluate output signals of the analog to digital converter.

Embodiments of the instant invention are directed to a microwave measurement device for a device for processing and measuring properties of a moving rod of tobacco of the tobacco processing industry, as described above. The device includes a microwave resonator structured and arranged so that the rod of material is conveyable through the microwave resonator, a microwave generator with an output frequency $f_0$, a frequency stabilized oscillator structured and arranged to generate an intermediate frequency $f_{IM}$ that is less than $f_0$, and a single sideband modulator structured and arranged to supply the microwave resonator with a sideband signal having a sideband frequency shifted with respect to the output frequency $f_0$ by the intermediate frequency $f_{IM}$. At least one analysis arrangement includes a connection in series of a single sideband demodulator, a low-pass filter, and an analog to digital converter, and the single sideband demodulator is structured and arranged to receive a measurement signal of the sideband frequency one of transmitted or reflected from the microwave resonator, and to receive the output frequency $f_0$. The low-pass filter is structured and arranged to pass an output signal of the single sideband demodulator with the intermediate frequency $f_{IM}$, and to filter out higher frequency signal portions.

Embodiments of the invention are directed to a method for processing and measuring properties of a moving rod of material of the tobacco processing industry. The method includes conveying the rod of material through a microwave resonator, generating an output frequency $f_0$, modulating the output frequency $f_0$ in a single sideband modulator with an intermediate frequency $f_{IM}$ that is less than $f_0$, and supplying a sideband signal with a sideband frequency $f_0+f_{IM}$ or $f_0-f_{IM}$ to the microwave resonator. The method also includes demodulating the signal of the sideband frequency $f_0+f_{IM}$ or $f_0-f_{IM}$ at least one of transmitted and reflected by the microwave resonator in a single sideband demodulator with a signal of the output frequency $f_0$, and passing a measurement signal portion with the intermediate frequency $f_{IM}$ through a low-pass filter to an analog to digital converter, while filtering out higher frequency signal portions.

According to embodiments of the invention, the method can include via a single sideband demodulation with the output frequency $f_0$, modulating a sideband signal of the sideband frequency $f_0+f_{IM}$ or $f_0-f_{IM}$, shielded from the microwave resonator through at least one of an insulator, a circulator, a directional coupler, and a signal divider, down to the intermediate frequency $f_{IM}$, which is then transferred via a second low-pass filter to a second analog to digital converter.

In accordance with other embodiments, the analog to digital converter, the second analog to digital converter, and an oscillator, which generates the intermediate frequency $f_{IM}$, are synchronized to a frequency stabilized time signal.

In accordance with still yet other embodiments of the present invention, the method can include controlling the sideband frequency by adjusting the output frequency $f_0$ to attain a resonance frequency in the microwave resonator. The control can utilize a phase of a transmitted signal, and a target phase value is zero. Further, the control can utilize the position of a maximum or minimum of the at least one of the transmitted and reflected signal. Moreover, the method can include periodically switching the output frequency between two values that are adapted so that the sideband frequency alternatingly lies above and below a resonance maximum or minimum, wherein a same signal amplitude at those frequencies is sought. A value of the slope of the resonance curve equal to zero is sought. Moreover, at least one of: with a measurement of an $S_{21}$ parameter, controlling the sideband frequency to a maximum signal amplitude, and with a measurement of the $S_{11}$ parameter, controlling the sideband frequency to a minimum signal amplitude.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 1:
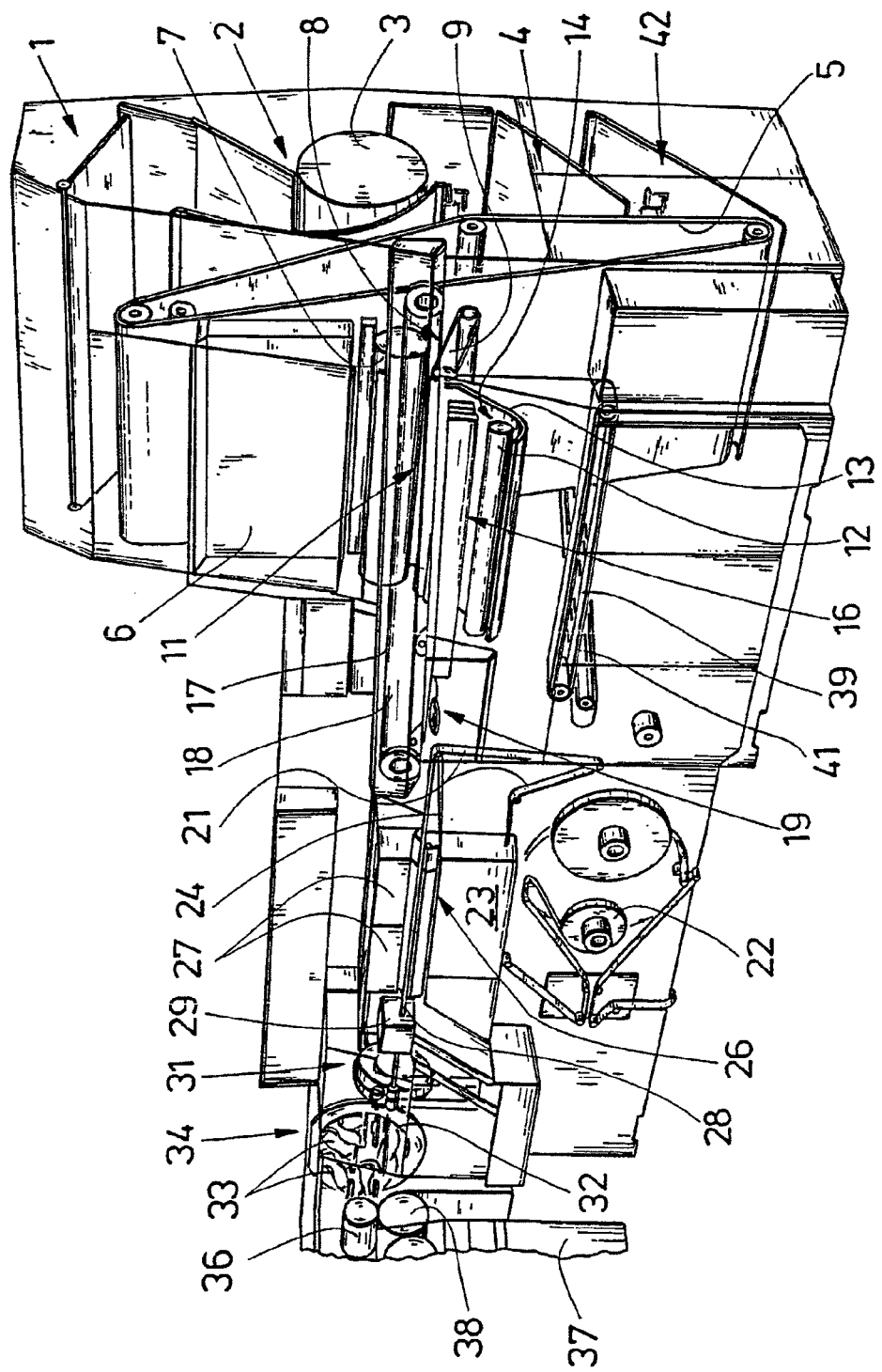
FIG. 1 illustrates a schematic design of a cigarette rod machine.

FIG. 1 illustrates the general design of a cigarette rod machine of the "PROTOS" type by Hauni Maschinenbau AG of Hamburg, Germany. A predistributor 2 is loaded in portions with loose tobacco from a sluice 1. Under control, a take-out roll 3 of the predistributor 2 replenishes a tank 4 with tobacco from which a steep-angle conveyor 5, designed as an endless belt, removes tobacco and supplies a bulking chute 6. From the bulking chute 6, a pin roller 7 removes a uniform stream of tobacco, which is beaten out of the pins of the pin roller 7 by a picker roller 8, and flings it onto an apron 9 guided as an endless belt and circulating with constant speed.

A tobacco carpet formed on the apron 9 is flung into a sieving device 11 which generates an air curtain that larger or heavy tobacco parts pass by, whereas all other tobacco particles are directed by the air stream of the air curtain into a hopper 14 formed by a pin roller 12 and a wall 13. From the pin roller 12, the tobacco is flung into a tobacco channel 16 against a rod conveyor 17 at which the tobacco is held by suction air in a vacuum pressure chamber 18, and is showered as an endless tobacco rod. A trimmer 19 which is substantially composed of a pair of rotating discs disposed in the plane of the transport direction of the endless tobacco rod, and a deflector, removes excess tobacco from the endless tobacco rod and cuts the endless tobacco rod formed in this manner to the desired thickness.

Next, the tobacco rod is placed on an endless strip of cigarette paper 21, pulled from a reel 22, guided at the same speed and is guided through a printing unit 23. The endless strip of cigarette paper 21 is placed on a driven garniture belt 24 that transports the endless tobacco rod and the endless strip of cigarette paper 21 through a forming device 26 in which the endless strip of cigarette paper is folded around the endless rod of tobacco so that an edge stands up which is glued in a known manner by a glue apparatus, not shown. Thereupon, the adhesive seam is closed and dried by a tandem seam sealer 27.

An endless cigarette rod 28 formed in this manner passes through rod density measurement device 29 that controls the trimmer 19, and is cut by a knife apparatus 31 into double length cigarettes 32. These are transferred by a transfer device 34 having controlled arms 33 into a receiving drum 36 of a filter assembler 37, on whose cutting drum 38 they are divided into individual cigarettes using a circular knife. Endless conveyor belts 39, 41 convey excess tobacco into a container 42 disposed beneath the tank 4, from which the returned tobacco is removed again by the steep-angle conveyor 5.

Figure 2:
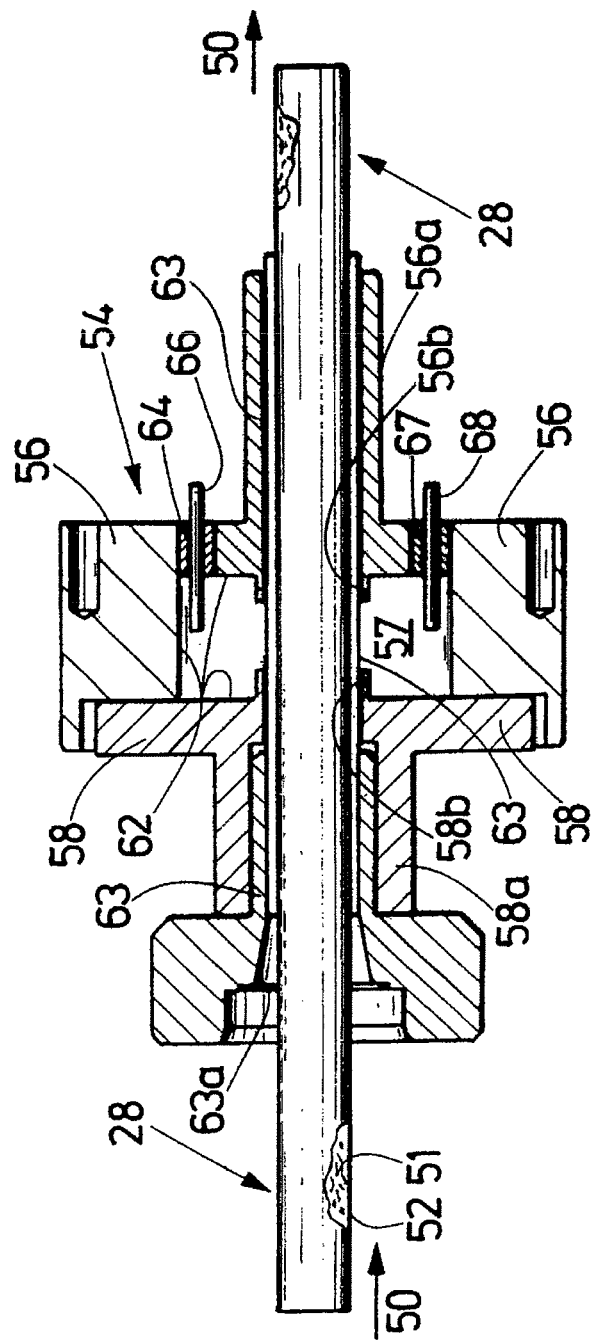
FIG. 2 illustrates a schematic cross-sectional representation through a microwave resonator.

FIG. 2 shows a schematic cross-sectional representation of a suitable resonator housing. An endless cigarette rod 28, partially broken open, moving in the direction of the arrow 50, consisting of a filler 51 and a wrapper 52 of cigarette paper, passes through the resonator housing 54, to which the microwaves are fed for the purpose of capturing at least one property of the filler 51, for example the mass or the moisture. The resonator housing 54 has a cavity in the shape of a hollow cylinder 56, with an interior or resonator cavity 57 being disposed symmetrically to the endless cigarette rod 28. For closing, a cover 58 is screwed to it.

The resonator cavity 57 of the resonator housing 54 can be vapor coated with a thin layer of gold 62, which reliably prevents the formation of corrosion that would adversely influence the measurement value constancy.

A protective pipe 63 that is preferably composed of a substance of the polyaryletherketone (PAEK) group, for example polyether ether ketone (PEEK), is used for mechanically closing of the resonator cavity 57 with respect to the endless cigarette rod 28, and to prevent contamination of the resonator cavity 57. The protective pipe 63 is widened in the shape of a funnel at one of its ends 63a, at which the endless rod 28 enters into the resonator housing 54.

Outside of the resonator cavity 57, the resonator housing 54 extends in a tubular shape (56a, 58a) outwards on both sides in the direction of the rod 28, in order to prevent the emission of microwaves from the resonator cavity 57. It also extends in a tubular shape (56b, 58b) inwards to some extent. A coupling in antenna 66 insulated from the hollow cylinder 56 by an insulating ring 64 serves for coupling in the microwaves generated by a microwave generator. A coupling out antenna 68 insulated from the hollow cylinder 56 by an insulator 67 serves to decouple microwaves which are to be supplied to an evaluation circuit, not shown.

The frequency of the introduced microwave signals is preferably selected so that at resonance the amplitude of the microwave field in the cavity 57 has a maximum in the center, i.e. at the location of the endless cigarette rod 28. If the introduced frequency does not correspond to the resonance frequency, the amplitude has a maximum at the location of a coupling in antenna 66 and decreases in the direction of the coupling out antenna 68. In the process, the amplitude of field decreases over the cross-section of the endless cigarette rod 28, that is, it is inhomogeneous.

Figure 3:
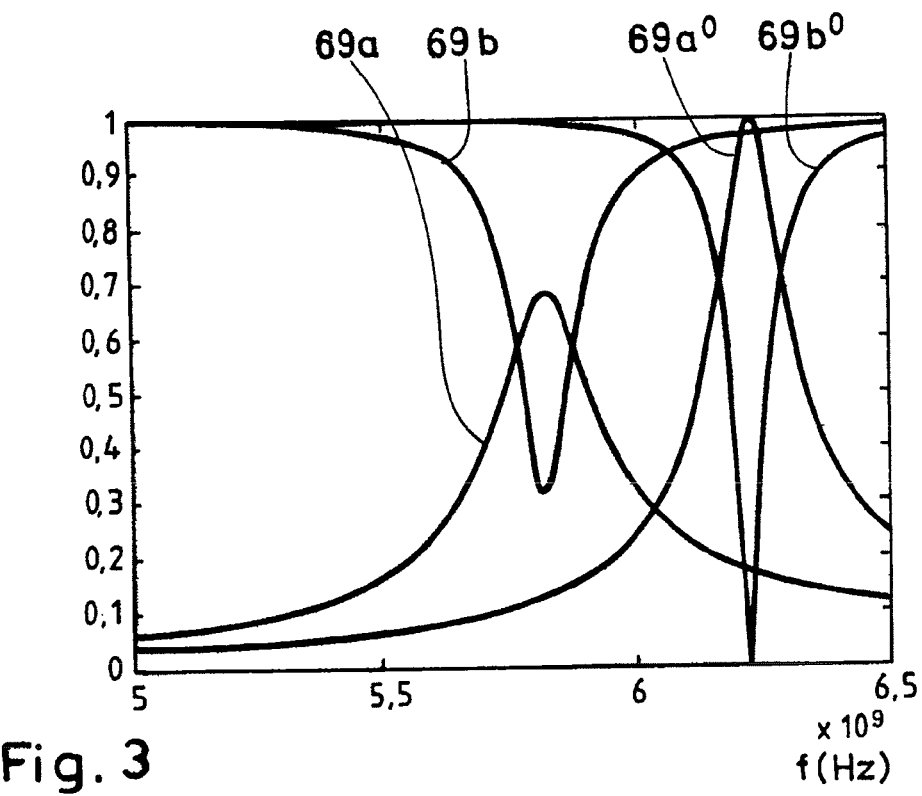
FIG. 3 illustrates a frequency-response curve of the amplitudes of the scattering parameters $S_{21}$ and $S_{11}$ in the cases of a filled and unfilled resonator.
Figure 4:
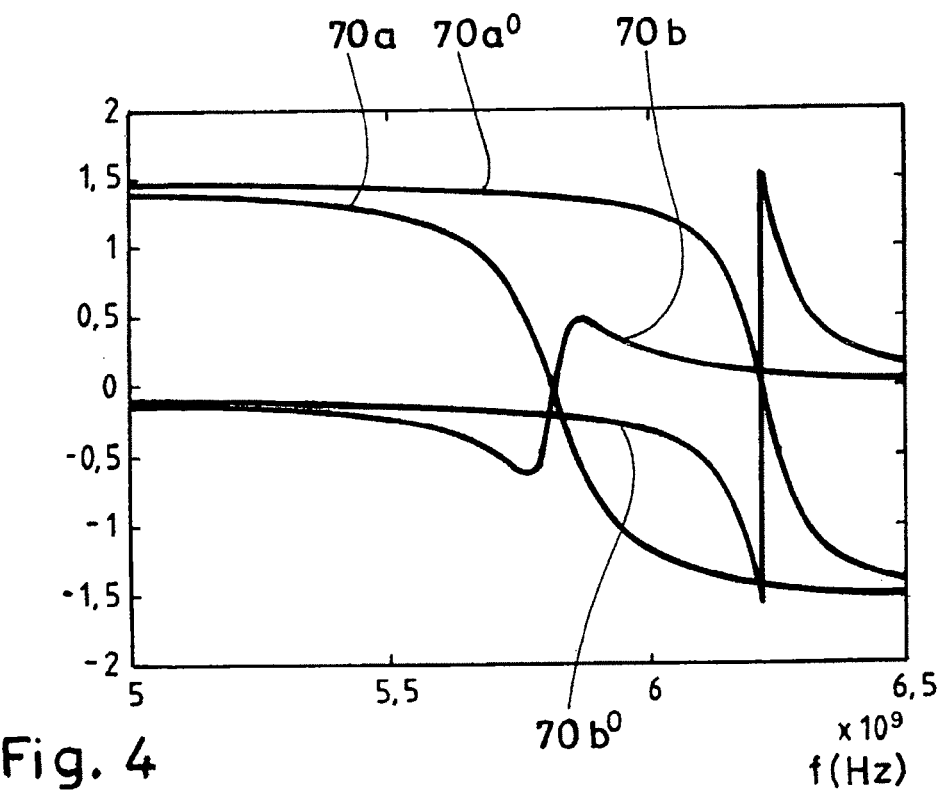
FIG. 4 illustrates the frequency-response curve of the phases of the scattering parameters $S_{21}$ and $S_{11}$ in the cases of a filled and unfilled resonator.

FIGS. 3 and 4 show the amplitudes and the phases of the scattering parameters $S_{11}$ and $S_{21}$ in a simulation. The X-axes represent the frequency of the introduced microwave signal and extend between 5 GHz and 6.5 GHz.

FIG. 3 shows, on the Y-axis, the relative amplitude with values between 0 and 1. Curves with the reference numbers $69a^0$ and $69b^0$ correspond to the unloaded resonator. Here, $69a^0$ represents the progressing of the frequency-dependent transmitted component, thus, the $S_{21}$ parameter, which has a maximum value of 1 at approximately 6.23 GHz. Thus, complete transmission prevails at this frequency. The corresponding reflection curve for the scattering parameter $S_{11}$, in the case of an unloaded resonator of infinite quality, with the reference number $69b^0$, has at this frequency a minimum with the value 0. Outside of this minimum, the parameter $S_{11}$ has a value near 1, therefore, nearly complete reflection prevails.

If the resonator is penetrated by an endless rod of material, for example an endless cigarette rod 28, the resonance frequency shifts to a lower frequency, to approximately 5.8 GHz in the represented example. This applies for both the $S_{21}$ parameter 69a as well as for the $S_{11}$ parameter 69b. At the same time, the two resonance curves broaden. Furthermore, the amplitude decreases at resonance. Thus, the curve of the $S_{21}$ parameter only attains a maximum of approximately 0.7, whereas the reflection, i.e. the $S_{11}$ parameter has a value of 0.3 at resonance.

It is not shown that in the loss-free case, i.e. the case without material in the resonator with infinite quality, the variable $(|S_{11}|^2+|S_{21}|^2)^{0.5}$ has the value 1 in the entire frequency range, whereas in the lossy case it has a value of less than 1 at resonance, where the minimum is attained at the resonance frequency. The difference to 1 is a measure for the power dissipation realized in the resonator. This value is always at a maximum at resonance.

FIG. 4 shows the frequency-response of phases of the resonance curves represented in FIG. 3 in the loaded and unloaded state. In the unloaded state, the phase $70a^0$ of the $S_{21}$ parameter, which at lower frequencies starts with the value $+\pi/2$, has a zero crossing at 6.23 GHz, while converging at higher frequencies towards the value $-\pi/2$. The corresponding $S_{11}$ phase parameter $70b^0$ starts at a low negative value and approaches the resonance frequency so that its value decreases towards $-\pi/2$. When crossing the resonance frequency the phase reverses and increases to the value $+\pi/2$. At still higher frequencies, the value decreases towards 0. With this, an ideal microwave resonator is assumed without any losses.

In the case of a loaded microwave resonator, a phase 70a of the $S_{21}$ parameters results whose zero crossing is shifted with respect to the unloaded case 70a⁰ towards a lower resonance frequency of approximately 5.8 GHz. Furthermore, the slope of the zero crossing is somewhat reduced. The phase 70b of the $S_{11}$ parameter is significantly changed compared to the unloaded case due to the broadening of the resonance and due to the loss in the resonator with the presence of an endless rod of material. In this case also, the S11 phase parameter 70b starts initially at lower frequencies with a slightly negative value, and upon nearing the resonance frequency takes on a strongly negative value. However, there is no reversal at the value $-\pi/2$ toward $+\pi/2$, rather a zero crossing occurs with a positive slope. Shortly after crossing through the zero line, the phase 70b of the $S_{11}$ parameter increases in the loaded case to a positive maximum at approximately 0.5, and then reverses and at high frequencies again trends towards 0. The zero crossings of the phase 70a of the $S_{21}$ parameter and the phase 70b of the $S_{11}$ parameter in the immediate the vicinity of the zero crossings are well-suited as a control variable for frequency tracking.

Figure 5:
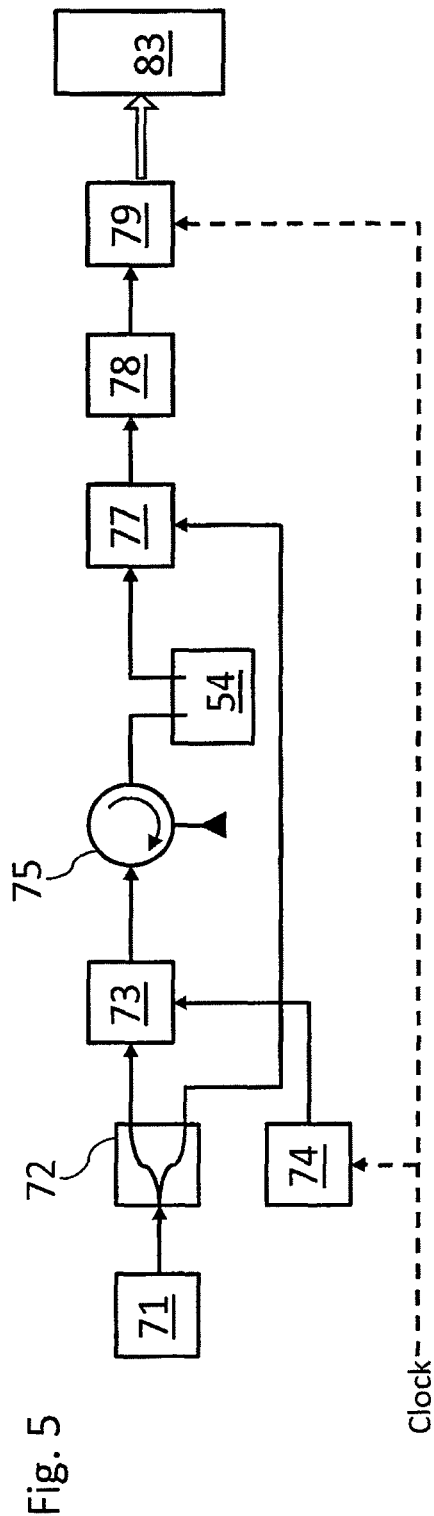
FIG. 5 illustrates a schematic circuit arrangement of a measurement device according to the invention.

FIG. 5 shows a first example of a circuit arrangement according to the invention for implementing a single side band modulation method. In a synthesizer or microwave generator 71 a microwave signal with a frequency $f_0$, of approximately 5.8 GHz for example, is generated as an output signal. The signal is divided in a coupler 72 into two in-phase signals. One of the signals is led to a single sideband modulator 73, whereas the other is led to a single sideband demodulator 77. An intermediate frequency signal with the intermediate frequency $f_{IM}$, which is significantly lower than $f_0$, at 10 MHz for example, generated by an intermediate frequency oscillator 74, is led to the single sideband modulator 73. The intermediate frequency signal is synchronized in the process to an externally supplied clock signal "clock".

The single sideband modulator generates a microwave signal with the frequency $f_0+f_{IM}$ or $f_0-f_{IM}$, which is led to a circulator 75. The circulator 75 passes the signal from the single sideband modulator 73 to an input port of a microwave resonator 54, whereas microwave power reflected from the input port of the microwave resonator 54 is deflected in the circulator 75 to a third output, which has a terminal load symbolized as a triangle which completely absorbs the reflected power. Therefore no reflected power is returned to the single side band modulator 73.

In the example shown in FIG. 5, an output port of the microwave resonator 54 is connected to the single sideband demodulator 77. In the single sideband demodulator 77, the output signal of the output port of the microwave resonator 54 with the frequency $f_0+f_{IM}$ or $f_0-f_{IM}$ is mixed with the output signal from the coupler 72 with the frequency $f_0$, and a signal with a significantly lower intermediate frequency $f_{IM}$ is generated, among others. It is led to the low-pass filter 78 for suppressing high-frequency signal portions, and in a sampling and digitalization stage, in particular an analog to digital converter 79 which is controlled by an external clock signal "clock", is converted into digital values. The synchronization signal is represented by a dashed line.

Due to the interaction of the single sideband modulator 73 and the single sideband demodulator 77, both the amplitude of the parameter $S_{21}$ and its phase are contained in the intermediate frequency signal $f_{IM}$ output from the single sideband demodulator 77 (see FIGS. 3 and 4). The parameter $S_{21}$ can be determined in magnitude and phase with the sampling circuit, which is synchronized with reference to the external clock signal.

Figure 6:
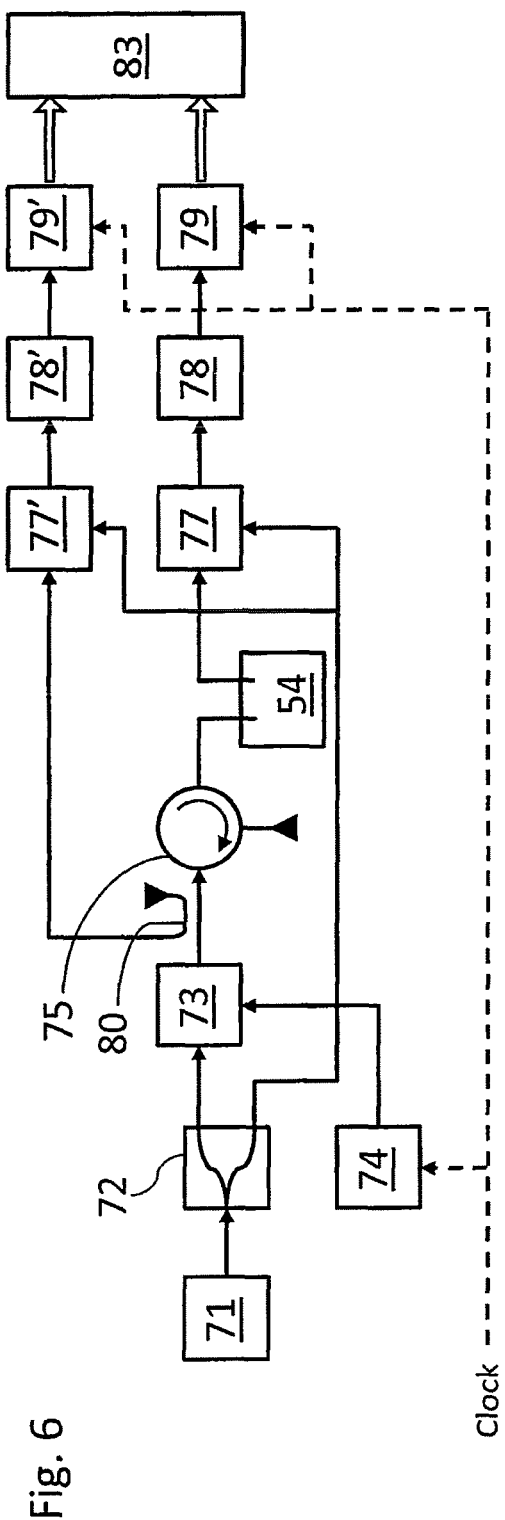
FIG. 6 illustrates a schematic circuit arrangement of a further measurement device according to the invention.

FIG. 6 shows a further circuit arrangement according to the invention, wherein now two analysis arrangements are shown having connections in series of single sideband demodulators, low-pass filters and analog to digital converters.

In contrast to FIG. 5 where only the transmitted signal was subjected to a corresponding single sideband demodulation, filtering and digitization, according to FIG. 6, the unchanged input signal of the resonator or the output signal from the single sideband modulator 73 is tapped with a directional coupler 80, and subjected to a corresponding evaluation in a single sideband demodulator 77', and low-pass filter 78', and an analog to digital converter 79'. For this purpose, the output signal with the frequency $f_0$ is split, and led to the two single sideband demodulators 77 and 77'. The synchronization signal "clock" is also led to both analog to digital converters 79, 79'. This way, the signal that contains the amplitude and phase of scattering parameter $S_{21}$, can be compared to the generated signal, so that possible changes in the signal, for example changes of the amplitude, can be computationally eliminated by calculating the ratio. The shift of the phase of the output signal can also be detected this way, and considered and corrected in the evaluation of the phase of the $S_{21}$ parameter.

Figure 7:
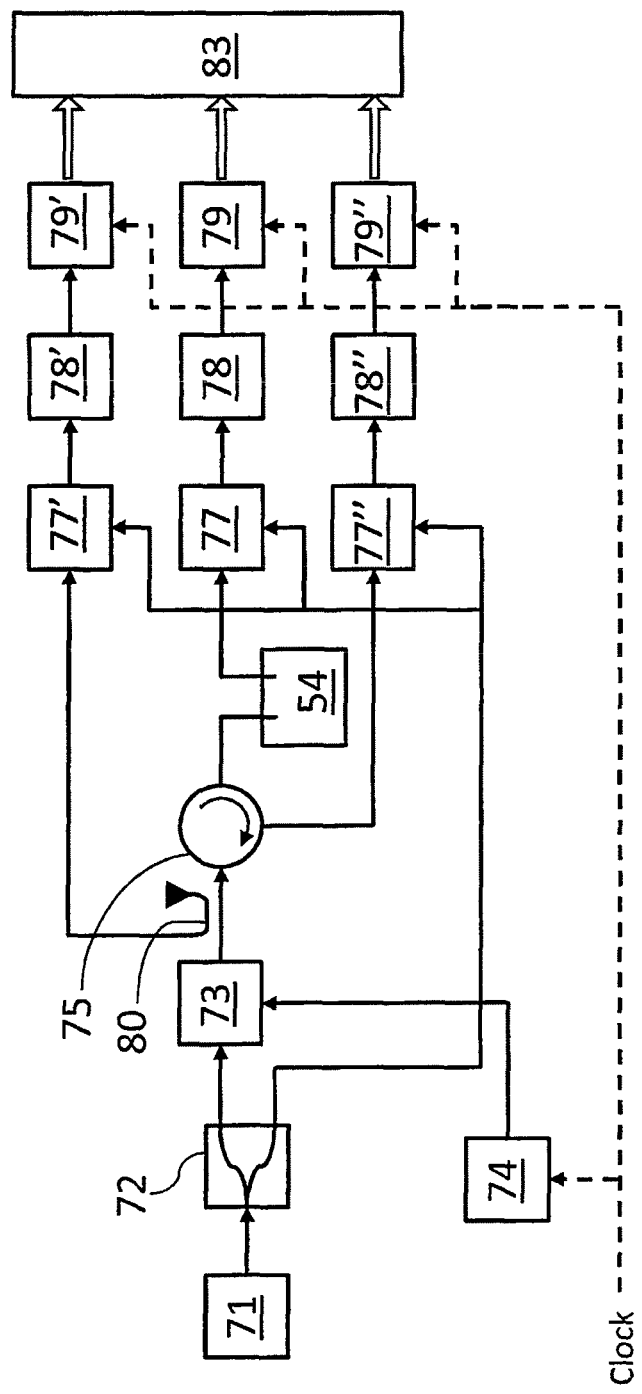
FIG. 7 illustrates a schematic circuit arrangement of a further measurement device according to the invention.

FIG. 7 shows a further development of the circuit arrangement from FIG. 6. In addition to the components represented in FIG. 6, a further analysis arrangement with a connection in series of a single sideband modulator 77", low-pass filter 78", and analog to digital converter 79" is represented, which receive measurement signals reflected by the microwave resonator 54 and singled out via the circulator 75, and subject it to a corresponding single sideband demodulation and the digitization. The single sideband demodulator 77" is also supplied with the signal $f_0$ from the coupler 72. The analog to digital converter 79" also receives the synchronization signal "clock".

The circuit arrangement shown in FIG. 7 makes it possible to determine the amplitude and the phase of both the scattering parameter $S_{21}$ and the scattering parameter $S_{11}$.

Figure 8:
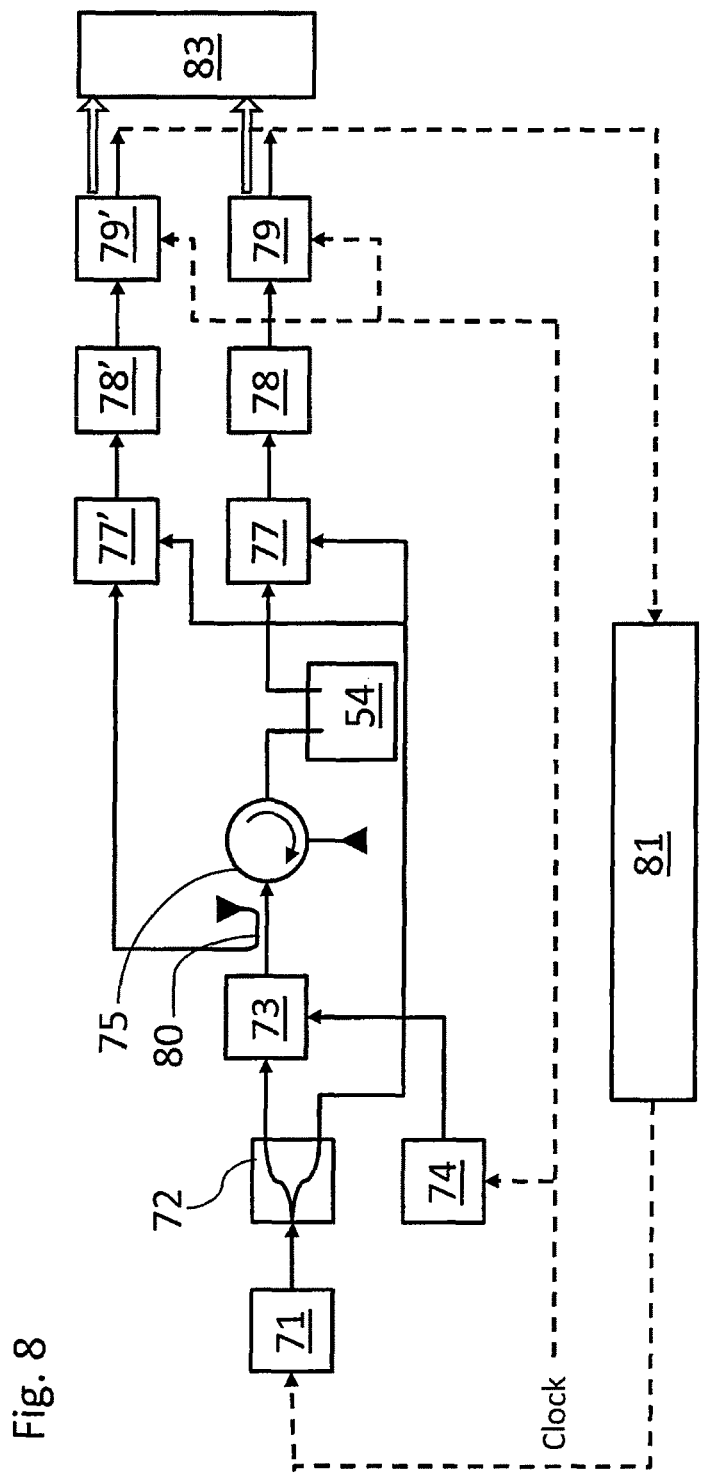
FIG. 8 illustrates a schematic circuit arrangement of a further measurement device according to the invention with frequency tracking.

FIG. 8 shows a further development of the circuit arrangement according to FIG. 6. In addition to the components represented in FIG. 6, a control device is provided in the form of a microprocessor 81 designed in particular as a digital signal processor, that receives the digitized measurement values determined by the analog to digital converters 79 and 79'. Because the microprocessor 81 contains all information about the current phase of the $S_{21}$ scattering parameter, the microprocessor 81 can control the microwave generator 71 and adapt its frequency $f_0$ so that phase is regulated to the zero crossing. Therefore, the microwave signal supplied to the microwave resonator 54 is always at the present resonance. This type of control is very fast and very accurate.

Figure 9:
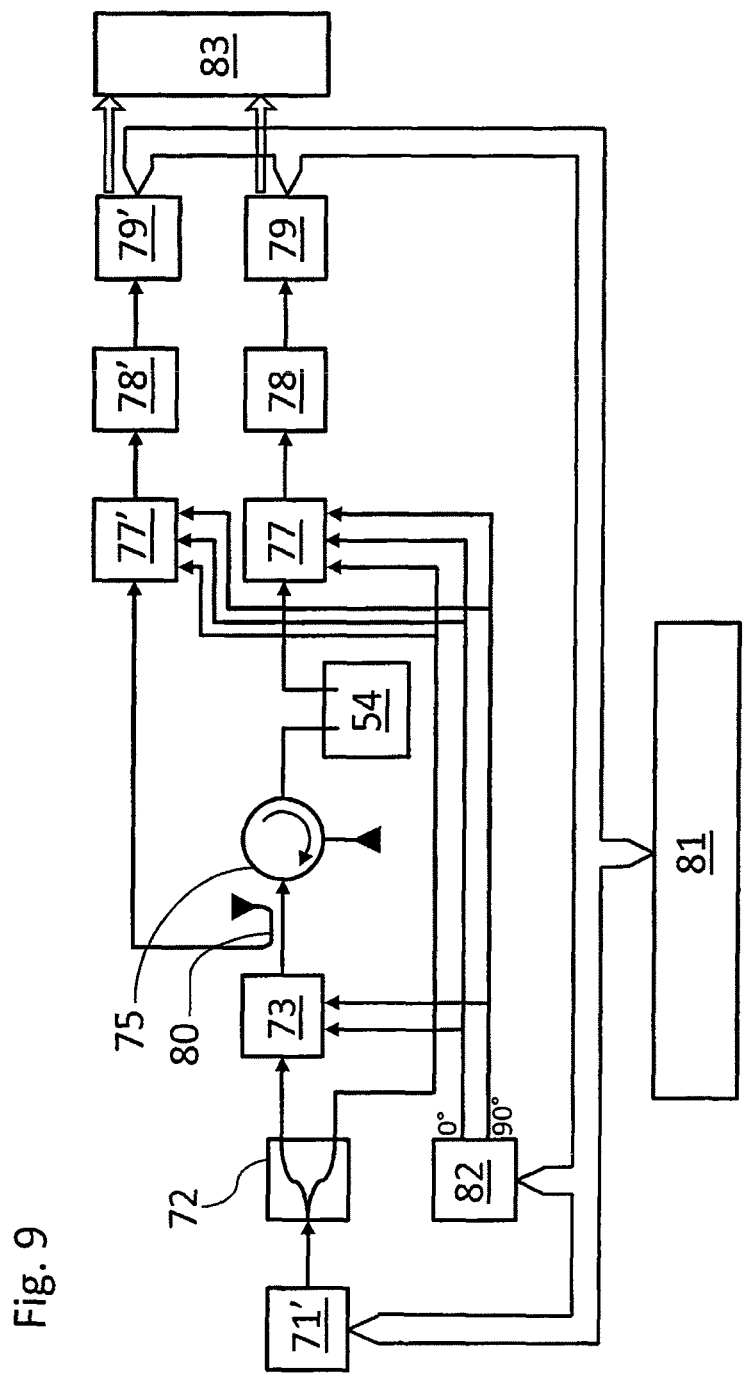
FIG. 9 illustrates a further schematic circuit arrangement of a measurement device according to the invention with frequency tracking.

FIG. 9 shows a schematic substantiation of an advantageous circuit arrangement. As already with FIG. 8, this is a circuit arrangement in which both the $S_{21}$ scattering parameter and the undisturbed input signal are analyzed, so that a drift in the input signal does not lead to an inaccuracy in the measurement. The frequency with the circuit arrangement of FIG. 9 is also tracked using the frequency $f_0$ from the microwave generator 71.

The microwave generator in FIG. 9 is designed as a DDS synthesizer 71', wherein DDS stands for "direct digital synthesis". This permits an extremely frequency and phase stable generation of microwave signals. The intermediate frequency is generated by a digital to analog converter 82, where two signals shifted by 90° with respect to each other are directly generated, which are required in the modulation and demodulation stages.

The single sideband modulator 73 is designed as an I/Q modulator, whereas the single sideband demodulators 77, 77' are designed as I/Q demodulators. This enables a particularly robust frequency and phase stable modulation and demodulation of the microwave signal. The I/Q modulation and demodulation represent a type of modulation in which an "in-phase component" ("I") and a "quadrature component" ("Q") are generated. Because the single sideband modulator 73 is supplied with the same input signals phase shifted by 0° and 90° as the single sideband demodulators 77 and 77', the phase position is determined unchangeably in this case. Therefore, measurement uncertainties in the phase position are excluded.

The digitized signals and control commands and synchronization signals are represented in FIG. 9 symbolically as a broad band, which connects the analog to digital converters 79, 79' to the microprocessor 81, to the intermediate frequency generator 82, and to the DDS synthesizer 71'.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims. Further, all named features, including those taken from the drawings alone, and individual features, which are disclosed in combination with other features, are considered individually and in combination as essential to the invention. Embodiments according to the invention can be satisfied through individual characteristics or a combination of several characteristics.

LIST OF REFERENCES 1 sluice
2 predistributor
3 take-out roller
4 tank
5 steep-angle conveyor
6 bulking chute
7 pin roller
8 picker roller
9 apron
11 sieving device
12 pin roller
13 wall
14 hopper
16 tobacco channel
17 rod conveyor
18 vacuum pressure chamber
19 trimmer
21 endless strip of cigarette paper
22 reel
23 printer
24 garniture tape
26 format
27 tandem seam sealer
28 endless cigarette rod
29 rod density measurement equipment
31 measurement apparatus
32 double length cigarettes
33 arm
34 transfer device
36 take-over drum
37 filter assembler
38 cutting drum
39 conveyor belt
41 conveyor belt
42 container
50 direction of movement
51 filler
52 wrapper
54 resonator housing
56 hollow cylinder
56a outer extension of the hollow cylinder 56
56b inner extension of the hollow cylinder 56
57 resonator cavity
58 cover
58a outer extension of the cover 58
58b inner extension of the cover 58
62 gold layer
63 protective pipe
63a protective pipe inlet
64 insulation ring
66 coupling antennae
67 insulation
68 decoupling antennae
69a amount $|S_{21}|$ of the loaded resonator housing
69a° amount $|S_{21}|$ of the unloaded resonator housing
69b amount $|S_{11}|$ of the loaded resonator housing
69b° amount $|S_{11}|$ of the unloaded resonator housing
70a phase ($S_{21}$) of the loaded resonator housing
70a° phase ($S_{21}$) of the unloaded resonator housing
70b phase ($S_{11}$) of the loaded resonator housing
70b° phase ($S_{11}$) of the unloaded resonator housing
71 microwave generator
71' DDS synthesizer
72 coupler
73 single sideband modulator
74 intermediate frequency oscillator
75 circulator
77, 77', 77" single sideband demodulator
78, 78', 78" low-pass filter
79, 79', 79" analog to digital converter
80 directional coupler
81 microprocessor
82 digital to analog converter
83 analysis device

What is claimed:

1. A device for processing and measuring properties of a moving rod of material of the tobacco processing industry that includes a microwave measurement device comprising:
a microwave resonator structured and arranged so that the rod of material is conveyable through the microwave resonator;
a microwave generator with an output frequency f0;
a frequency stabilized oscillator structured and arranged to generate an intermediate frequency fim that is less than f0;
a single sideband modulator structured and arranged to supply the microwave resonator with a sideband signal having a sideband frequency shifted with respect to the output frequency f0 by the intermediate frequency fim;
at least one analysis arrangement comprising a single sideband demodulator, a low-pass filter, and an analog to digital converter arranged in series;
the single sideband demodulator is coupled to receive a measurement signal of the sideband frequency that is transmitted through or reflected from the microwave resonator, and to receive the output frequency f0;
the low-pass filter is structured and arranged to pass an output signal of the single sideband demodulator with the intermediate frequency fim to the analog to digital converter, and to filter out higher frequency signal portions;
at least one of an insulator, a circulator, a directional coupler, and a signal divider being disposed between the single sideband modulator and the microwave resonator;
a control device structured and arranged to control the output frequency f0 so that the single sideband frequency tracks a present resonance frequency in the microwave resonator;
wherein the microwave generator comprises a digital signal generating device structured and arranged to generate the output frequency f0 by direct digital synthesis, and
wherein the single sideband modulator comprises an I/Q modulator, the single sideband demodulator comprises an I/Q demodulator supplied with the intermediate frequency fim, and the frequency stabilized oscillator comprises a digital to analog converter structured and arranged to generate two signals shifted from each other by 90° for the intermediate frequency fim;
an evaluation device structured and arranged to evaluate output signals of the analog to digital converter; and
wherein the control device comprises another evaluation device structured and arranged to evaluate output signals of the analog to digital converter.

2. The device according to claim 1, wherein the control device utilizes as a control variable at least one of a phase value and an amplitude of the transmitted or reflected signal, wherein a target for the control variable is at least one of a phase value of zero and an amplitude maximum or an amplitude minimum.

3. A device for processing and measuring properties of a moving rod of material of the tobacco processing industry that includes a microwave measurement device comprising:
a microwave resonator structured and arranged so that the rod of material is conveyable through the microwave resonator;
a microwave generator with an output frequency f0;
a frequency stabilized oscillator structured and arranged to generate an intermediate frequency fim that is less than f0;
a single sideband modulator structured and arranged to supply the microwave resonator with a sideband signal having a sideband frequency shifted with respect to the output frequency f0 by the intermediate frequency fim;
at least two analysis arrangements, each of the at least two analysis arrangements comprising a single sideband demodulator, a low-pass filter, and an analog to digital converter arranged in series,
wherein each single sideband demodulator of the at least two analysis arrangements is coupled to receive a measurement signal of the sideband frequency that is transmitted through or reflected from the microwave resonator, and to receive the output frequency f0;
wherein each low-pass filter of the at least two analysis arrangements is structured and arranged to pass an output signal of the respective single sideband demodulator with the intermediate frequency fim to the respective analog to digital converter, and to filter out higher frequency signal portions,
wherein a first of the at least two analysis arrangements is structured and arranged to receive a measurement signal transmitted by the microwave resonator, and a second of the at least two analysis arrangements is structured and arranged to receive a measurement signal reflected by the microwave resonator;
at least one of an insulator, a circulator, a directional coupler, and a signal divider being disposed between the single sideband modulator and the microwave resonator;
a control device structured and arranged to control the output frequency f0 so that the single sideband frequency tracks a present resonance frequency in the microwave resonator;
an evaluation device structured and arranged to evaluate output signals of the analog to digital converters; and
wherein the control device comprises another evaluation device structured and arranged to evaluate output signals of the analog to digital converters.

4. The device according to claim 3,
wherein the microwave generator comprises a digital signal generating device structured and arranged to generate the output frequency f0 by direct digital synthesis, and
wherein the single sideband modulator comprises an I/Q modulator, the single sideband demodulator comprises an I/Q demodulator supplied with the intermediate frequency fim and the frequency stabilized oscillator comprises a digital to analog converter structured and arranged to generate two signals shifted from each other by 90° for the intermediate frequency fim.

5. The device according to claim 3, wherein the control device utilizes as a control variable at least one of a phase value and an amplitude of the transmitted or reflected signal, wherein a target for the control variable is at least one of a phase value of zero and an amplitude maximum or an amplitude minimum.

6. A device for processing and measuring properties of a moving rod of material of the tobacco processing industry that includes a microwave measurement device comprising:
a microwave resonator structured and arranged so that the rod of material is conveyable through the microwave resonator;
a microwave generator with an output frequency f0;
a frequency stabilized oscillator structured and arranged to generate an intermediate frequency fim that is less than f0;
a single sideband modulator structured and arranged to supply the microwave resonator with a sideband signal having a sideband frequency shifted with respect to the output frequency f0 by the intermediate frequency fim;
at least two analysis arrangements, each of the at least two analysis arrangements comprising a single sideband demodulator, a low-pass filter, and an analog to digital converter arranged in series,
wherein each single sideband demodulator of the at least two analysis arrangements is coupled to receive a measurement signal of the sideband frequency that is transmitted through or reflected from the microwave resonator, and to receive the output frequency f0,
wherein each low-pass filter of the at least two analysis arrangements is structured and arranged to pass an output signal of the respective single sideband demodulator with the intermediate frequency fim to the respective analog to digital converter and to filter out higher frequency signal portions, wherein a first of the at least two analysis arrangements is structured and arranged to receive a measurement signal transmitted by the microwave resonator, and a second of the at least two analysis arrangements is structured and arranged to receive a measurement signal reflected by the microwave resonator;

at least one of an insulator, a circulator, a directional coupler, and a signal divider being disposed between the single sideband modulator and the microwave resonator;

another analysis arrangement comprising a single sideband demodulator, a low-pass filter, and an analog to digital converter arranged in series, wherein the single sideband demodulator of the another analysis arrangement is structured and arranged to receive a decoupled part of a sideband signal via the at least one of the circulator, the insulator, the directional coupler, and the signal divider, and to receive the output frequency f0, and wherein the low-pass filter of the another analysis arrangement is structured and arranged to pass an output signal of the respective single sideband demodulator with the intermediate frequency fim to the respective analog to digital converter, and to filter out higher frequency signal portions; and a control device structured and arranged to control the output frequency f0 so that the single sideband frequency tracks a present resonance frequency in the microwave resonator, wherein the control device comprises an evaluation device structured and arranged to evaluate output signals of the analog to digital converters.

7. The device according to claim 6, further comprising another evaluation device structured and arranged to evaluate output signals of the analog to digital converters.

8. The device according to claim 6, wherein the control device utilizes as a control variable at least one of a phase value and an amplitude of the transmitted or reflected signal, wherein a target for the control variable is at least one of a phase value of zero and an amplitude maximum or an amplitude minimum.

9. The device according to claim 6,
wherein the microwave generator comprises a digital signal generating device structured and arranged to generate the output frequency f0 by direct digital synthesis, and
wherein the single sideband modulator comprises an I/Q modulator, the single sideband demodulator comprises an I/Q demodulator supplied with the intermediate frequency fim, and the frequency stabilized oscillator comprises a digital to analog converter structured and arranged to generate two signals shifted from each other by 90° for the intermediate frequency fim.

10. A method for processing and measuring properties of a moving rod of material of the tobacco processing industry, comprising:
conveying the rod of material through a microwave resonator;
generating an output frequency f0;
modulating the output frequency f0 in a single sideband modulator with an intermediate frequency fim that is less than f0;
supplying a sideband signal with a sideband frequency f0+fim or f0−fim to the microwave resonator;
demodulating a signal of the sideband frequency f0+fim or f0−fim at least one of transmitted through and reflected by the microwave resonator in a single sideband demodulator with a signal of the output frequency f0; and
passing a measurement signal portion with the intermediate frequency fim through a low-pass filter to an analog to digital converter, while filtering out higher frequency signal portions;
controlling the sideband frequency by adjusting the output frequency f0 so that the single sideband frequency tracks a present resonance frequency in the microwave resonator; and
periodically switching the output frequency between two values that are adapted so that the sideband frequency alternatingly lies above and below a resonance maximum or minimum, wherein a same signal amplitude at those frequencies is sought.

11. The method according to claim 10, further comprising, via a single sideband demodulation with the output frequency f0, demodulating a sideband signal of the sideband frequency f0+fim or f0−fim, shielded from the microwave resonator through at least one of an insulator, a circulator, a directional coupler, and a signal divider, down to the intermediate frequency fim, which is then transferred via a second low-pass filter to a second analog to digital converter.

12. The method according to claim 10, wherein the control utilizes a phase of a transmitted signal, and a target phase value is zero.

13. The method according to claim 10, wherein a value of the slope of the resonance curve equal to zero is sought.

14. The method according to claim 10, wherein, at least one of:
with a measurement of an $S_{21}$ parameter, controlling the sideband frequency to a maximum signal amplitude, and
with a measurement of the $S_{11}$ parameter, controlling the sideband frequency to a minimum signal amplitude.

* * * * *